United States Patent
Poolman et al.

(10) Patent No.: US 10,422,734 B2
(45) Date of Patent: Sep. 24, 2019

(54) THERMAL COMPENSATION

(71) Applicant: Malvern Panalytical Limited, Malvern, Worcestershire (GB)

(72) Inventors: Rhys Poolman, Malvern (GB); David Stringfellow, Malvern (GB); Nigel Lightfoot, Malvern (GB); Jason Cecil William Corbett, Malvern (GB)

(73) Assignee: Malvern Panalytical Limited, Malvern, Worcestershire (GB)

( * ) Notice: Subject to any disclaimer, the term of this patent is extended or adjusted under 35 U.S.C. 154(b) by 0 days.

(21) Appl. No.: 15/668,552

(22) Filed: Aug. 3, 2017

(65) Prior Publication Data
US 2018/0038782 A1    Feb. 8, 2018

(30) Foreign Application Priority Data

Aug. 4, 2016    (EP) .................................. 16182896

(51) Int. Cl.
*G01N 15/00* (2006.01)
*G01N 21/00* (2006.01)
(Continued)

(52) U.S. Cl.
CPC ....... *G01N 15/0211* (2013.01); *G01N 21/532* (2013.01); *G01N 2015/0222* (2013.01);
(Continued)

(58) Field of Classification Search
None
See application file for complete search history.

(56) References Cited

U.S. PATENT DOCUMENTS 3,457,419 A * 7/1969 Rosa ................. G01F 1/661
250/207
3,575,050 A * 4/1971 Lynnworth ............... G01F 1/66
73/861.27
(Continued)

FOREIGN PATENT DOCUMENTS

GB  2340936  3/2000
JP  2015-141025  8/2015

OTHER PUBLICATIONS

Novales, Bruno. "Diffraction in Particle Size Analysis", Encyclopedia of Analytical Chemistry, 2006.*
(Continued)

*Primary Examiner* — Shawn Decenzo
*Assistant Examiner* — Jarreas C Underwood
(74) *Attorney, Agent, or Firm* — Morrison & Foerster LLP

(57) ABSTRACT

Method of characterizing particles suspended in a fluid dispersant by light diffraction, comprising: obtaining measurement data from a detector element, the detector element being arranged to measure the intensity of scattered light; identifying a measurement contribution arising from light scattered by inhomogeneities in the dispersant; processing the measurement data to remove or separate the measurement contribution arising from light scattered by inhomogeneities in the dispersant; calculating a particle size distribution from the processed measurement. The detector element is one of a plurality of detector elements from which the measurement data is obtained. The detector elements are arranged to measure the intensity of scattered light at a plurality of scattering angles, the plurality of scattering angles distributed over a plurality of angles about an illumination axis. Identifying a measurement contribution arising from light scattered by inhomogeneities in the dispersant
(Continued)

comprises identifying measured scattered light that is asymmetric about the illumination axis.

13 Claims, 4 Drawing Sheets

(51) Int. Cl.
G01N 15/02 (2006.01)
G01N 21/53 (2006.01)
G01N 21/47 (2006.01)

(52) U.S. Cl.
CPC ............. G01N 2021/4716 (2013.01); G01N 2021/4721 (2013.01)

(56) References Cited

U.S. PATENT DOCUMENTS

| | | | |
|---|---|---|---|
| 3,966,332 A * | 6/1976 | Knapp | G01N 21/9009 356/427 |
| 4,385,830 A * | 5/1983 | Webb | G01P 5/01 356/28 |
| 4,984,889 A | 1/1991 | Sommer | |
| 5,133,602 A | 7/1992 | Batchelder et al. | |
| 5,416,580 A * | 5/1995 | Trainer | G01N 15/0211 356/336 |
| 5,475,235 A * | 12/1995 | Phillips | H01S 5/042 250/574 |
| 6,191,853 B1 | 2/2001 | Yamaguchi et al. | |
| 6,519,033 B1 * | 2/2003 | Quist | G01N 15/14 356/337 |
| 6,781,688 B2 * | 8/2004 | Kren | G01N 21/9501 356/237.1 |
| 7,471,393 B2 | 12/2008 | Trainer | |
| 7,990,525 B2 * | 8/2011 | Kanda | G01N 21/51 356/73 |
| 2003/0076494 A1 | 4/2003 | Bonin et al. | |
| 2008/0218738 A1 * | 9/2008 | Trainer | G01B 11/08 356/72 |

OTHER PUBLICATIONS

Extended European Search Report dated Feb. 10, 2017, directed to EP Application No. 16182896.7; 10 pages.

* cited by examiner

THERMAL COMPENSATION

CROSS-REFERENCE TO RELATED APPLICATION

This application claims priority to European Application No. 16182896.7, filed on Aug. 4, 2016, the content of which is incorporated herein by reference in its entirety.

FIELD OF THE INVENTION

The invention relates to a particle characterization instrument, and to a method of particle characterization.

BACKGROUND OF THE INVENTION

A diffraction based particle characterization instrument works by measuring light scattered from particles. A mathematical description (or model) of the relationship between scattering patterns and particle size distribution is used to infer the particle size distribution. The mathematical description may require, as a calculation parameter, the ratio of refractive index between the particle and the medium in which the particle is suspended. By comparing measured light scattering data to the model a particle size distribution (PSD) may be calculated. The theory that is typically used assumes that the refractive index of the medium is homogenous and static. If the refractive index of the medium is not homogeneous and static during measurement the calculated PSD may include spurious sizes.

Both diffraction based measurements (such as static light scattering) and dynamic light scattering (based on temporal characteristics of scattering) are affected by scattering from inhomogeneities in the diluent medium.

There are several reasons the refractive index of the suspending medium (or dispersant) may be inhomogeneous. The most common is due to thermal variations in the dispersant but other causes can include pressure variations, contaminants, sample dissolution, etc. The scattering pattern caused by these kinds of inhomogeneities may be substantially random in nature, and therefore difficult to remove from measurement data.

JP2015/141025 discloses a device in which isotropic background light is subtracted to allow a scattering measurement to be performed without a filter to remove fluorescent light. U.S. Pat. No. 7,471,393 discloses an instrument for measuring the size distribution of a particle sample by counting and classifying particles into selected size ranges.

Conventionally, the effect of thermal or pressure variations are minimised by waiting for such variations to equalize while holding the sample in a temperature controlled environment. However, conditions can exist where this takes an excessive amount of time or even where settling will not occur. For contaminants or dissolution there is no known general solution.

SUMMARY OF THE INVENTION

According to a first aspect of the invention, there is provided a method of characterizing particles suspended in a fluid dispersant by light diffraction, comprising:

obtaining measurement data from a detector element, the detector element arranged to measure the intensity of scattered light;

identifying a measurement contribution arising from light scattered by inhomogeneities in the dispersant;

processing the measurement data to remove or separate the measurement contribution arising from light scattered by inhomogeneities in the dispersant;

calculating a particle size distribution from the processed measurement.

The detector element may be one of a plurality of detector elements from which the measurement data is obtained.

The detector elements may be arranged to measure the intensity of scattered light at a plurality of scattering angles, the plurality of scattering angles distributed over a plurality of angles about an illumination axis Calculating a particle size distribution may comprise performing a calculation based on the diffraction pattern of light at different angles (e.g. static light scattering), and/or may comprise performing an autocorrelation on the measurement data (e.g. dynamic light scattering).

Identifying a measurement contribution arising from light scattered by inhomogeneities in the dispersant may comprise identifying measured scattered light that is asymmetric about the illumination axis.

Identifying measured scattered light that is asymmetric about the illumination axis may comprise identifying whether the scattered light is sufficiently asymmetric about the illumination axis to suggest that it does not arise from scattering from a particle. A small degree of asymmetry about the illumination axis may not mean that light is scattered from a dispersant inhomogeneity. Identifying measured scattered light that is asymmetric about the illumination axis may comprise any data processing that identifies data that is more asymmetric than would be expected to arise from scattering from a particle.

In some embodiments the method need not include actually performing the measurement that provides the measurement data. Obtaining the measurement data may include reading the measurement data from a storage medium (e.g. non-volatile memory, flash drive, hard disk, etc.) or receiving the measurement data over a communications network.

At least some of the plurality of scattering angles may be alternately arranged between a first and second radial location about the illumination axis with increasing scattering angle.

The detector elements must be sensitive to asymmetry about the illumination axis. The first and second radial location about the illumination axis may be separated by at least 90 degrees about the illumination axis.

Viewed along the illumination axis, each detector element may be considered to lie on a radius drawn from the illumination axis through the centroid of the detector element. The location of the detector element along the illumination axis is not relevant to determining the degree of angular separation about illumination axis, so the respective radial locations of the detectors can be considered with reference to their projection on a virtual plane, normal to the illumination axis, at an arbitrary location. The degree of angular separation between respective detector elements is therefore the angle between their respective radial locations in the virtual plane.

At least some of the plurality of scattering angles may be a logarithmic series of scattering angles. At least some of the detector elements may be arranged with their centroids in a logarithmic series of scattering angles.

Obtaining a measurement may comprise obtaining a time history of the intensity of scattered light from the detector element, or from the detector elements (e.g. at the plurality of scattering angles).

Identifying a measurement contribution arising from light scattered by inhomogeneities in the dispersant may comprise identifying peaks in the measurements for each of the plurality of scattering angles.

Identifying peaks may comprise comparing measurement data with a smoothed data (such as a moving average, or filtered data) obtained from the same measurement data.

Where the smoothed data comprises a moving average, the moving average may be obtained from a plurality of moving averages with different temporal width.

The method may comprise classifying the peaks as: a particle peak, resulting from scattering from a particle; or a spurious peak, resulting from scattering from dispersant inhomogeneities.

A combination of temporal and symmetry characteristics can be used to identify and reject spurious peaks.

The method may comprise classifying a peak as a particle peak when corresponding peaks are present within a period $t_w$ over a continuous range of n detectors with adjacent scattering angles, at least some of the n detectors having angular separation about the illumination axis.

Processing the data may comprise discarding measurement data taken at times when a measurement contribution arising from light scattered by inhomogeneities in the dispersant is present. The data discarded may comprise only those scattering angles that include a measurement contribution arising from light scattered by inhomogeneities in the dispersant.

Processing the data may comprise removing a spurious peak by replacing the spurious peak with a moving average.

The method may further comprise performing a diffraction experiment (including illuminating a sample and detecting scattered light) to obtain the measurement data.

According to a second aspect, there is provided a processor or instrument configured to perform the method of the first aspect.

According to a third aspect, there is provided a machine readable, non-transient storage medium, comprising instructions for configuring a processor or instrument to perform the method according to the first aspect.

Features of each and every aspect may be combined with those of each and every other aspect.

BRIEF DESCRIPTION OF THE DRAWINGS

Embodiments will be described, purely by way of example, with reference to the accompanying drawings, in which.

DETAILED DESCRIPTION OF THE INVENTION

Figure 1:
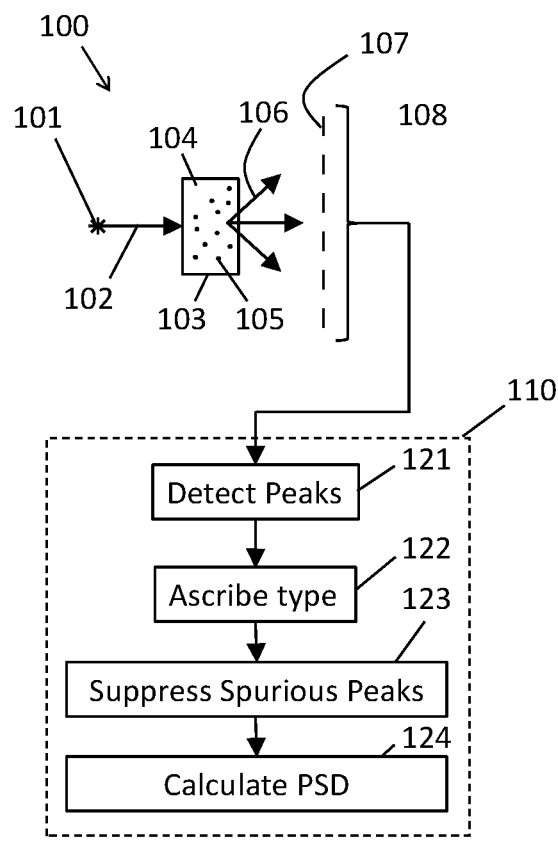
FIG. 1 is a schematic drawing of a particle characterization instrument configured in accordance with an embodiment.

Referring to FIG. 1, a laser diffraction particle characterization instrument 100 is shown, comprising a light source 101, sample cell 103, detector 107 and processor 110. The light source 101 may be a laser source, and is operable to illuminate a sample within the sample cell 103 along an illumination axis 102. The sample comprises particles 105 suspended in a dispersant fluid 104 (e.g. water).

The interaction of the illuminating light beam with the particles 105 results in scattering/diffraction, producing scattered light 106. The detector 107 is arranged to detect the scattered light. A plurality of detector elements are provided, arranged to receive light scattered at different scattering angles (relative to the illumination axis 102). The detector elements 107 are also distributed about the illumination axis 102 at different angles. The detector 107 may comprise an array of detector elements (e.g. a focal plane array detector) or may comprise a plurality of discrete (e.g. spaced apart) detector elements.

The scatter pattern projected from the particles 105 onto the detector 107 is symmetric about the illumination axis 102 for particle sizes where polarisation effects are insignificant. In practice this typically means that the scatter pattern is symmetric about the illumination axis for particle sizes greater than about 10 μm.

Figure 2:
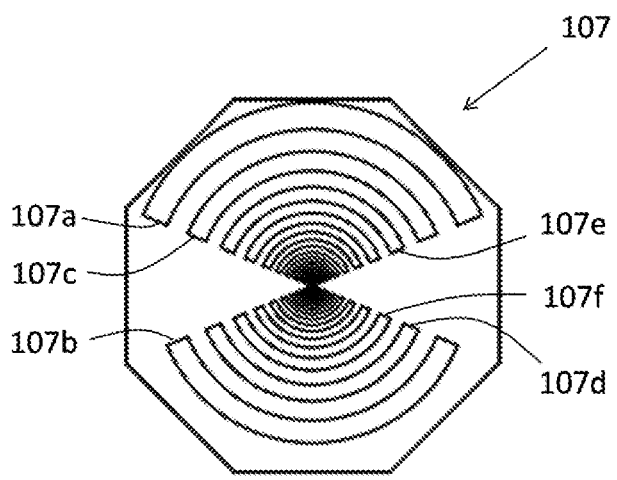
FIG. 2 is a schematic of a detector array.

Referring to FIG. 2, an example detector focal plane array 107 is shown, comprising a plurality of detector elements 107a-f (only the larger elements are labelled for clarity). The detector elements are alternately arranged between a first and second angle about the illumination axis 102 with increasing scattering angle. In the example of FIG. 2, the first and second angle about the illumination axis 102 are 180 degrees apart (i.e. located on opposite sides of the illumination axis 102). In the present example, the highest scattering angle detector element 107a is above the beam axis, the next element 107b is below, the next element 107c is above, and so on. The detector elements in this example are annular, and span an angle about the illumination axis 102 of at least 100 degrees, but less than 180 degrees. Spatially separating the detector elements associated with adjacent scattering angles reduces electrical crosstalk and improves the overall fidelity of the measurement data 108.

The detector elements 107a-f may be centred on scattering angles corresponding with a logarithmic sequence, and successive detector elements may increase in width (extent in scattering angle) logarithmically as the scattering angle increases. Near to the illumination axis 102, at small scattering angles, there may be many closely spaced detectors, and at larger scattering angles there may be fewer but larger detectors. Such an arrangement may be advantageous, because larger particles produce a higher intensity of scattered light that is at low scattering angles, and smaller particles produce a reduced intensity of scattered light that is more isotropic (i.e. includes high scattering angles).

The measurement data from the detector 107 may arranged in scattering angle order, providing a continuous and smooth scattered energy distribution as a particle traverses the laser beam. The intensity with respect to time and scattering angle may be used to create a 3-dimensional visualization of the scattering peak from a particle as it traverses the illumination beam. Despite the alternating detector locations, such a scattering peak will be smooth, due to the symmetric scattering about the illumination axis 102. Scattering resulting from a dispersant inhomogeneity will instead produce a peak which is not smooth with respect to scattering angle, because of the separation of the detector elements for adjacent scattering angles about the illumination axis and the asymmetric scattering about the illumination axis.

Although the detector of FIG. 2 may be particularly suitable for detecting asymmetry in scattered light patterns, any arrangement of detector elements that is capable of detecting asymmetry about the illumination axis is also suitable (for example a 2D array of pixel elements).

Figure 3:
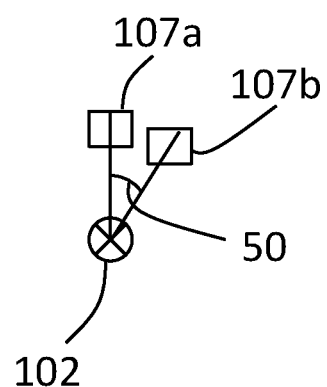
FIG. 3 is a diagram illustrating angular separation of detector elements about the illumination axis.

FIG. 3 illustrates that measurement of an angle of separation 50 about the illumination axis 102, with reference to a first detector element 107a and a second detector element 107b. The angle of separation 50 is determined with reference to an angle between a first vector between the illumination axis 102 and a centroid of the first detector element 107a and a second vector between the illumination axis 102 and a centroid of the second detector element 107b. The first and second sensor element 107a, 107b are not necessarily at the same location along the illumination axis: if the vectors are offset along the illumination axis the angle can be determined with reference to the projection of the vectors onto a virtual plane that is normal to the illumination axis.

Returning to FIG. 1, the detector 107 is operable to detect the scattered light 106, and to output measurement data 108, which may provide a time history of the intensity of scattered light at each detector element. The measurement data 108 is provided to a processor 110.

The processor 110 executes instructions that may be loaded into a memory. The processing device 110 may include any suitable number(s) and type(s) of processors or other devices in any suitable arrangement. Example types of processing devices 110 include microprocessors, microcontrollers, digital signal processors, field programmable gate arrays, application specific integrated circuits, and discrete circuitry.

The memory represents any structure(s) capable of storing and facilitating retrieval of information (such as data, program code, and/or other suitable information on a temporary or permanent basis). The memory may represent a random access memory, read only memory, hard drive, Flash memory, optical disc, or any other suitable volatile or non-volatile storage device(s).

The processor 110 is configured to identify a measurement contribution arising from light scattered by inhomogeneities in the dispersant 104 by identifying measured scattered light that is anisotropic about the illumination axis, and to process the measurement data 108 to remove this measurement contribution. The processor 110 subsequently calculates a PSD from the processed measurement data.

In the present example, the processor 110 is configured to identify peaks (at 121) in the measurement data 108, and to subsequently ascribe a type to each peak (at 122): a particle peak, arising from light scattered from a particle; or a spurious peak, arising from scattering from a dispersant inhomogeneity. The processor 110 processes the measurement data 108 to suppress the spurious peaks (as 123), and then determines a PSD from the processed measurement data (at 124).

Peaks in time resolved data 108 may be identified by comparing the data for each detector element with a moving average of the data for that detector element.

The moving average $\mu_j(t)$ at time t may be calculated as:

$$\mu_j(t) = \frac{\int_{t-\Delta t}^{t} I_j(t)dt}{\Delta t}$$

where $\Delta t$ is the length of the time window over which the integration is calculated and $I_j(t)$ the intensity on detector element j.

The standard deviation $\sigma_j(t)$ at time t may be calculated as:

$$\sigma_j(t) = \sqrt{\int_{t-\Delta t}^{t} I_j^2(t)dt - \mu_j^2(t)}$$

where $\Delta t$ should be the same window used to calculate $\mu_j(t)$.

The moving average value may be compared to the raw data by using a normalised difference, $\Delta_j(t)$:

$$\Delta_j(t) = \frac{|I_j(t) - \mu_j(t)|}{\mu_j(t)}$$

and compared to a criteria value C. Alternatively, a z-score, $\Delta'_j(t)$ can be used to compare the moving average to the raw data:

$$\Delta'_j(t) = \frac{I_j(t) - \mu_j(t)}{\sigma_j(t)}$$

If $\Delta_j(t) > C$ or $\Delta'_j(t) > C$ then the maximum point in the range t to $t+\Delta t$ is a peak in the data, caused either by a particle or an inhomogeneity of the refractive index of the suspending medium.

The parameter $\Delta t$ defines the sensitivity of the method to the life-time of the peak in the raw measurement data, which may be dependent on the viscosity of the dispersant and the hydrodynamic coupling between the particles 105 and the dispersant 105. If the peak has a life time larger than $\Delta t$ then it will not be detected. To avoid failing to detect peaks arising from slow moving particles, several moving averages may be used with different window sizes. To improve the speed of peak identification, the moving averages may be calculated in parallel.

The moving average smooths out the smaller fluctuations so that the comparison $\Delta_j(t)$ can be calculated. In general, any smoothing algorithm may be used. For example, another simple smoothing method that might be used is exponential smoothing, the simplest form of which would be $$s_j(t) = \alpha I_j(t) + (1-\alpha) s_j(t-\delta t)$$

where $s_j(t)$ is the smoothed data on detector element j, $0<\alpha<1$ is the smoothing factor and $\delta t$ is the time step of the detector element. In the comparison defined by $\Delta_j(t)$ the function $s_j(t)$ would replace the function $\mu_j(t)$. Other examples of smoothing functions include autoregressive moving averages and autoregressive integrated moving averages.

Next, the identified peaks are ascribed as either particle peaks, due to light scattering from particles; or spurious peaks, arising from light scattering due to dispersant inhomogeneity (resulting in refractive index variations). The light scattering due to particles occurs over angular ranges broad enough to extend over multiple detector elements, and is generally sufficiently symmetric about the central point of the detector 107 to be detected across a continuous range of detector elements (in terms of scattering angle progression).

This means that one way to characterize particle peaks is to check for peaks within the range t to $t+\Delta t$ over n detectors (n>1) and if present can attribute the cause of the peak to light scattering from particles. If this is not the case then a peak is categorised as a spurious peak, that is due to refractive index inhomogeneities.

The life time of the peaks may be determined as well as their position. With this extra information spurious peaks could be removed from the data and the data stitched back together. Another method of spurious peak identification would be to detect peaks in the background measurement phase, when no particles are present, as described above. All of these peaks would be spurious peaks (since no particles are present). The spurious peaks could be statistically analyzed to determine a typical life time of a spurious peak, and this could be compared with the peaks identified during the measurement. Those peaks that match the characteristics of spurious peaks could be categorized as due to refractive index inhomogeneities of the dispersant.

In some embodiments, measurement data 108 may be processed to remove a measurement contribution arising from light scattering from dispersant inhomogeneities. One way to remove the data is to exclude measurement data from detector elements corresponding with spurious peaks.

An alternative to identifying peaks in the data is to perform a frequency analysis on scattering data from a sample with substantially no particles (and an identical or representative dispersant). A filter may be generated based on the frequency analysis, to filter out fluctuations from the detector elements arising from dispersant inhomogeneities (as the data is obtained, or as a post-processing operation).

In some embodiments, a combination of asymmetry and temporal characteristics may be used to remove or separate a scattering contribution arising from dispersant inhomogeneities. For example, the output from the data may be filtered (to remove data with certain temporal characteristics) and then processed to identify asymmetric scattering. Alternatively, spurious peaks may be identified based on a combination of temporal and symmetry criteria. In some embodiments, both predetermined temporal characteristics and asymmetric scattering may be required to reject a peak as spurious.

Figure 4:
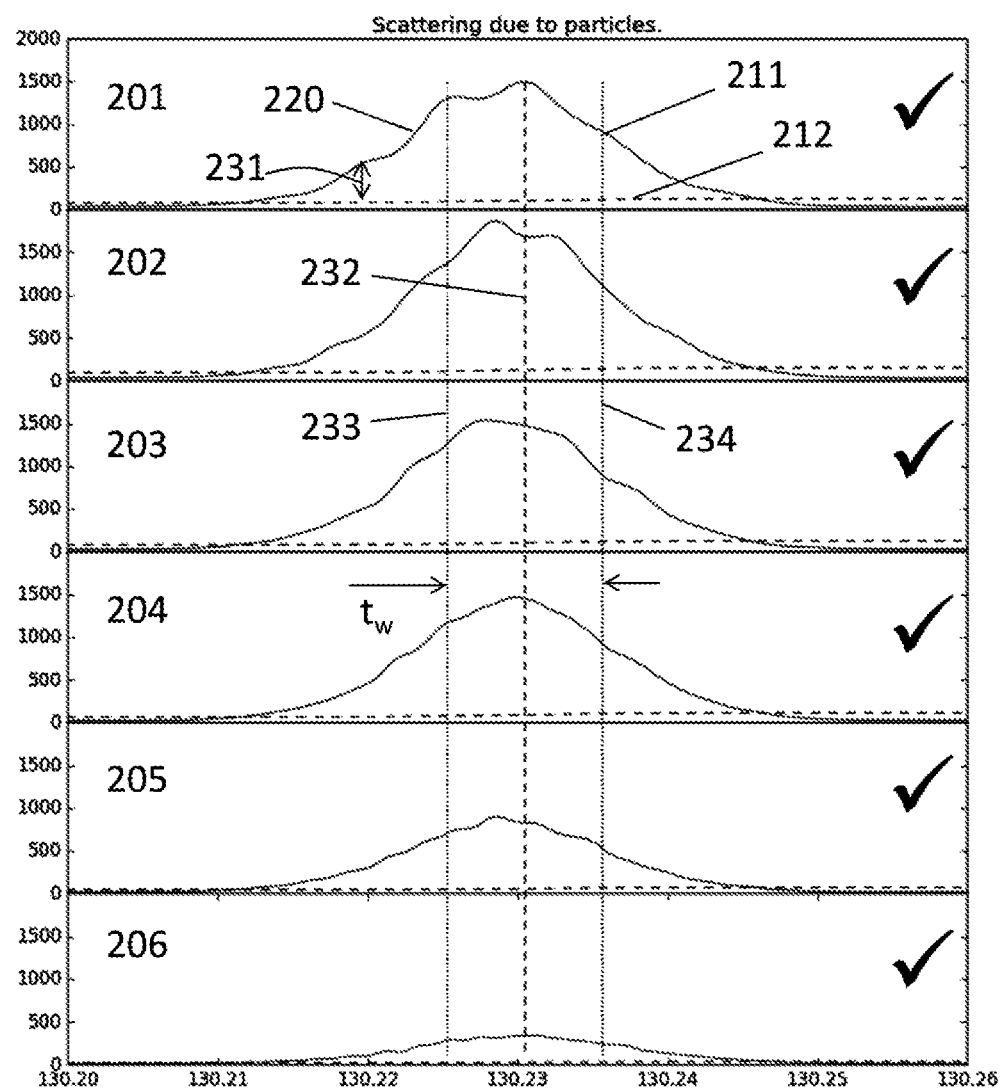
FIG. 4 illustrates the identification of a particle peak in measurement data.

FIG. 4 illustrates example scattering measurement data from a particle. Graphs 201-206 each display measurement data from a sequence of six detector elements that span a range of scattering angles. At least some of these six detectors are arranged in a different radial location about the illumination axis to at least some of the other detectors. Specifically, in this example, detectors providing odd numbered graphs 201, 203, 205, are on the opposite side of the illumination axis 102 to the detectors providing the even numbered graphs 202, 204, 206.

Each graph 201-206 includes raw measurement data 211 and a moving average 212. A peak 220 is detected in the first graph, due to the difference between the raw data 211 and moving average exceeding a threshold 231. The peak 220 has a maximum 232. A time window $t_w$ may be calculated around the maximum, with lower bound 233 and upper bound 234. In each of the other graphs 202-206, a peak is found within this time window. The peaks in each of these graphs 220 can therefore be categorised as particle peaks, resulting from light scattering from a particle.

Other criteria may be used to search for corresponding peaks. For example, the time window $t_w$ could start from the moment that the threshold is exceeded in graph 201, until the moment the threshold is not exceeded. The number of adjacent detectors to be checked to establish that the peak is a particle peak may be any appropriate number (e.g. 2, 3, 4, 5, 10, etc.), in this example 6.

Figure 5:
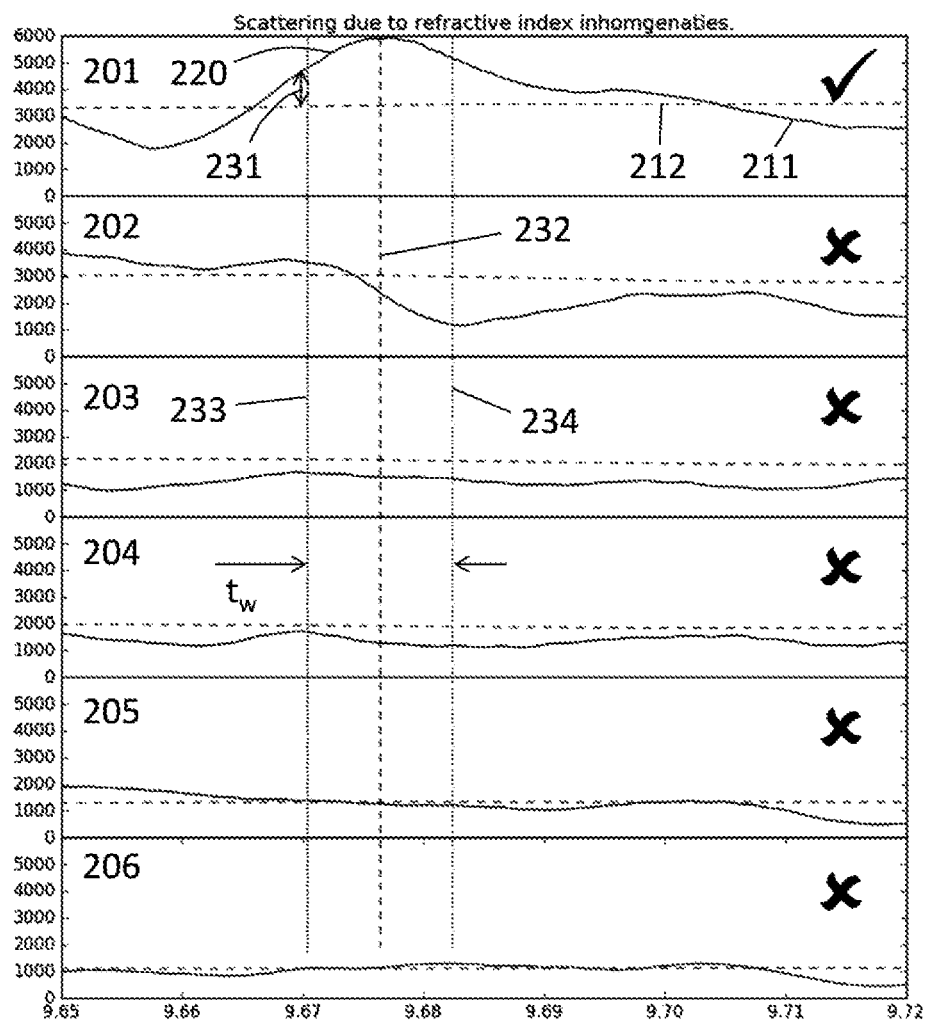
FIG. 5 illustrates the identification of a spurious peak in measurement data.

FIG. 5 shows example scattering measurement data from a dispersant inhomogeneity. A peak 220 is identified in the first graph 201, but no corresponding peak is present in the second graph 202, or any of the other graphs 203 to 206. The peak 220 is therefore categorized as a spurious peak. The measurement data may be processed to eliminate the spurious peak, for example by using the moving average value as the data for the duration of the spurious peak.

The ability to categorize peaks in the measurement data 108 on the basis of source (spurious or particle) allows several applications, the most important of which is isolated scattering data associated with particles. In doing so, spurious sizes will no longer be reported to the user of the particle sizing instrument. In general, the signal-to-noise ratio is also improved, so that accuracy of a PSD is improved.

The ability to separate data in the way described above may have several other applications. These include a "smart clean" application that would check for the presence and type of contaminants and then apply the appropriate cleaning procedure or to remove or reduce signals arising from the contaminants by algorithmic means. A "reduced sample size" mode may also be enabled, in which the required amount of sample is reduced because sources of noise could be removed from the data. The detection of bubbles in the dispersant could also be arranged and trigger a degassing procedure.

Another possible application would be a dynamic background monitor, which would allow the background to be monitored during a sample measurement rather than only before the measurement begins. The laser light used to illuminate the particles in the cell also produces a constant signal across each pixel, which is called the background. This is measured before the sample is measured and subtracted from the scattering values recorded by the detector after the sample is measured, which prevents the background influencing the PSD. It's possible that long time scale variations of this background during the measurement of the sample cause the subtraction of the background to be inaccurate. By monitoring the background during the measurement, a real time background may be subtracted. More accurate monitoring of the background is enabled when spurious peaks can be subtracted from the measurement data.

Although specific examples have been described, these are not intended to be limiting, and the skilled person will understand that further variations are possible within the scope of the invention, which is defined by the appended claims.

The invention claimed is:

1. A method of characterizing particles suspended in a fluid dispersant by light diffraction, comprising:
   obtaining measurement data from a detector element arranged to measure the intensity of scattered light;
   identifying a measurement contribution arising from light scattered by inhomogeneities in the dispersant;
   processing the measurement data to remove or separate the measurement contribution arising from light scattered by inhomogeneities in the dispersant;
   calculating a particle size distribution from the processed measurement;
   wherein:
   the detector element is one of a plurality of detector elements from which the measurement data is obtained;
   the detector elements are arranged to measure the intensity of scattered light at a plurality of scattering angles, the plurality of scattering angles distributed over a plurality of angles about an illumination axis; and
   identifying a measurement contribution arising from light scattered by inhomogeneities in the dispersant comprises identifying measured scattered light that is asymmetric about the illumination axis.

2. The method of claim 1, wherein at least some of the plurality of scattering angles are alternately arranged between a first and second radial location about the illumination axis with increasing scattering angle.

3. The method of claim 2, wherein the first and second radial location about the scattering axis are separated by at least 90 degrees about the illumination axis.

4. The method of claim 1, further comprising performing a diffraction experiment to obtain the measurement data.

5. The method of claim 1, wherein at least some of the detector elements are arranged with their centroids in a logarithmic series of scattering angles.

6. The method of claim 1, wherein obtaining a measurement comprises obtaining a time history of the intensity of scattered light from the detector element or the detector elements.

7. The method of claim 6, wherein identifying a measurement contribution arising from light scattered by inhomogeneities in the dispersant comprises identifying peaks in the measurements for each of the plurality of scattering angles.

8. The method of claim 7, wherein identifying peaks comprises comparing measurement data with smoothed data obtained from the same measurement data.

9. The method of claim 7, comprising classifying the peaks as a particle peak, resulting from scattering from a particle, or a spurious peak, resulting from scattering from dispersant inhomogeneities.

10. The method of claim 8, wherein the smoothed data comprises a moving average obtained from a plurality of moving averages with different temporal width.

11. The method of claim 9, comprising classifying a peak as a particle peak when corresponding peaks are present within a period $t_w$ over continuous range of n detectors with adjacent scattering angles, at least some of the n detectors having angular separation about the illumination axis.

12. A processor or instrument configured to perform the method of claim 1.

13. A machine readable, non-transient storage medium, comprising instructions for configuring a processor or instrument to perform the method of claim 1.

\* \* \* \* \*